US010021483B2

(12) United States Patent
Funakoshi

(10) Patent No.: US 10,021,483 B2
(45) Date of Patent: Jul. 10, 2018

(54) SOUND CAPTURE APPARATUS, CONTROL METHOD THEREFOR, AND COMPUTER-READABLE STORAGE MEDIUM

(71) Applicant: CANON KABUSHIKI KAISHA, Tokyo (JP)

(72) Inventor: Masanobu Funakoshi, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 547 days.

(21) Appl. No.: 14/534,035

(22) Filed: Nov. 5, 2014

(65) Prior Publication Data

US 2015/0139433 A1 May 21, 2015

(30) Foreign Application Priority Data

Nov. 15, 2013 (JP) ................................ 2013-237350

(51) Int. Cl.

*A61F 11/06* (2006.01)
*G10K 11/16* (2006.01)
*H03B 29/00* (2006.01)
*H04R 3/04* (2006.01)
*H04R 3/00* (2006.01)

(52) U.S. Cl.

CPC ............... *H04R 3/04* (2013.01); *H04R 3/005* (2013.01)

(58) Field of Classification Search

CPC ......... H04R 3/005; H04R 1/1083; H04R 3/04
USPC ................................................ 381/71.1, 94.1
See application file for complete search history.

(56) References Cited

U.S. PATENT DOCUMENTS 8,428,275 B2 4/2013 Yoshida et al.
2006/0262943 A1* 11/2006 Oxford .................. H04R 3/005 381/92
2011/0013075 A1* 1/2011 Kim ....................... H04N 5/602 348/370
2013/0035933 A1* 2/2013 Hirohata ................. G10L 15/20 704/206

FOREIGN PATENT DOCUMENTS

JP 2003-241787 A 8/2003
JP 2009-055583 A 3/2009

OTHER PUBLICATIONS

Japanese Office Action dated Aug. 28, 2017 in Japanese Patent Application No. 2013237350.

* cited by examiner

*Primary Examiner* — Paul S Kim
(74) *Attorney, Agent, or Firm* — Fitzpatrick, Cella, Harper & Scinto

(57) ABSTRACT

A noise signal is estimated based on a captured audio signal captured from a sound capture unit. It is determined whether the estimated noise signal thus estimated is in a noiseless state. If it is determined that the estimated noise signal is in the noiseless state, the captured audio signal is analyzed as a target sound signal, and a characteristic obtained by the analysis is learned and modeled, thereby generating a target sound model.

20 Claims, 9 Drawing Sheets

SOUND CAPTURE APPARATUS, CONTROL METHOD THEREFOR, AND COMPUTER-READABLE STORAGE MEDIUM

BACKGROUND OF THE INVENTION

Field of the Invention

The present invention relates to a sound capture technique for recording ambient sounds while suppressing a wind noise.

Description of the Related Art

With the recent spread of image capture apparatuses such as a camcorder, a camera, and a smartphone, it has become possible to easily capture images. In addition, many portable audio recorders capable of high-quality recording are also put into practical use. Accordingly, there has been an increase in opportunities to record ambient sounds or the sound from a target object outdoors, regardless of whether or not any image accompanies.

In the case of capturing sounds outdoors in this way, when a noise generated by the wind acting on a sound capture microphone (hereinafter referred to as “wind noise”) is mixed with a captured audio signal, the target sound becomes difficult to hear or become an annoying sound. Therefore, the removal or suppression of the wind noise has been an important issue.

Analysis of the frequency characteristics of the wind noise shows that much of the energy is localized in a low-frequency range of 500 Hz or less. Therefore, one example of the conventional techniques for suppressing the wind noise is a method that suppresses the wind noise by using a high-frequency band pass filter (hereinafter, referred to as “high-pass filter”).

However, with the wind noise suppression method using a high-pass filter, when the level of the wind noise is large, the amount of suppression of the high-pass filter needs to be increased accordingly. This poses the problem that the entire low-frequency range of the target sound component is suppressed, thus altering the tone of the target sound.

Another example of the conventional techniques for suppressing the wind noise is a method in which the suppression is achieved by estimating a wind noise signal and performing spectral subtraction based on a captured audio signal.

However, with the suppression method using spectral subtraction as well, there is the problem that the target sound component is drown out if the level of the wind noise becomes too large, and the subtraction of the wind noise also eliminates the target sound component.

Therefore, there is a conventional technique by which a target sound component that is lost by wind noise suppression processing is restored after the wind noise suppression, and the target sound component is supplemented.

For example, according to Japanese Patent Laid-Open No. 2009-55583, an input signal is separated into three bands of low, middle, and high frequency bands, and restoration signals from the middle band to the low band are generated. The restoration signals are mixed with a low-band signal of the input signal after estimating the level of the influence of the wind noise. Additionally, the middle-band signal is mixed after reducing the signal level. Techniques have been disclosed by which the wind noise is reduced with this configuration while suppressing the occurrence of a distortion.

However, the technique disclosed in Japanese Patent Laid-Open No. 2009-55583 uses middle-band and high-band signals, which have harmonicity, to restore the fundamental waves and low-order harmonics, and is problematic in that it can only restore the signals having harmonicity. Moreover, with this technique, there is no information for specifying the fundamental waves, and the level balance of the low-order harmonics is not considered. Accordingly, inaccurate low-band components may be added, and there is the possibility that the sound quality may be degraded, or the tone may be altered.

SUMMARY OF THE INVENTION

The present invention provides a sound capture technique that can prevent tone alteration and loss of target sound components, while suppressing noise, thereby performing precise restoration of a target sound.

To achieve the foregoing object, a sound capture apparatus according to the present invention includes the following configuration. That is, the sound capture apparatus is a sound capture apparatus that suppresses a noise contained in a captured audio signal captured from a sound capture unit, and outputs a target sound, including: an estimation unit configured to estimate a noise signal from the captured audio signal captured from the sound capture unit; a detection unit configured to detect whether an estimated noise signal estimated by the estimation unit is in a noiseless state; and a learning unit configured to, if the detection unit detects that the estimated noise signal is in the noiseless state, analyze the captured audio signal as a target sound signal, and learn and model a characteristic obtained by the analysis, thereby generating a target sound model.

According to the present invention, it is possible to prevent tone alteration and loss of target sound components, while suppressing noise, thereby performing precise restoration of a target sound.

Further features of the present invention will become apparent from the following description of exemplary embodiments (with reference to the attached drawings).

DESCRIPTION OF THE EMBODIMENTS

Figure 1:
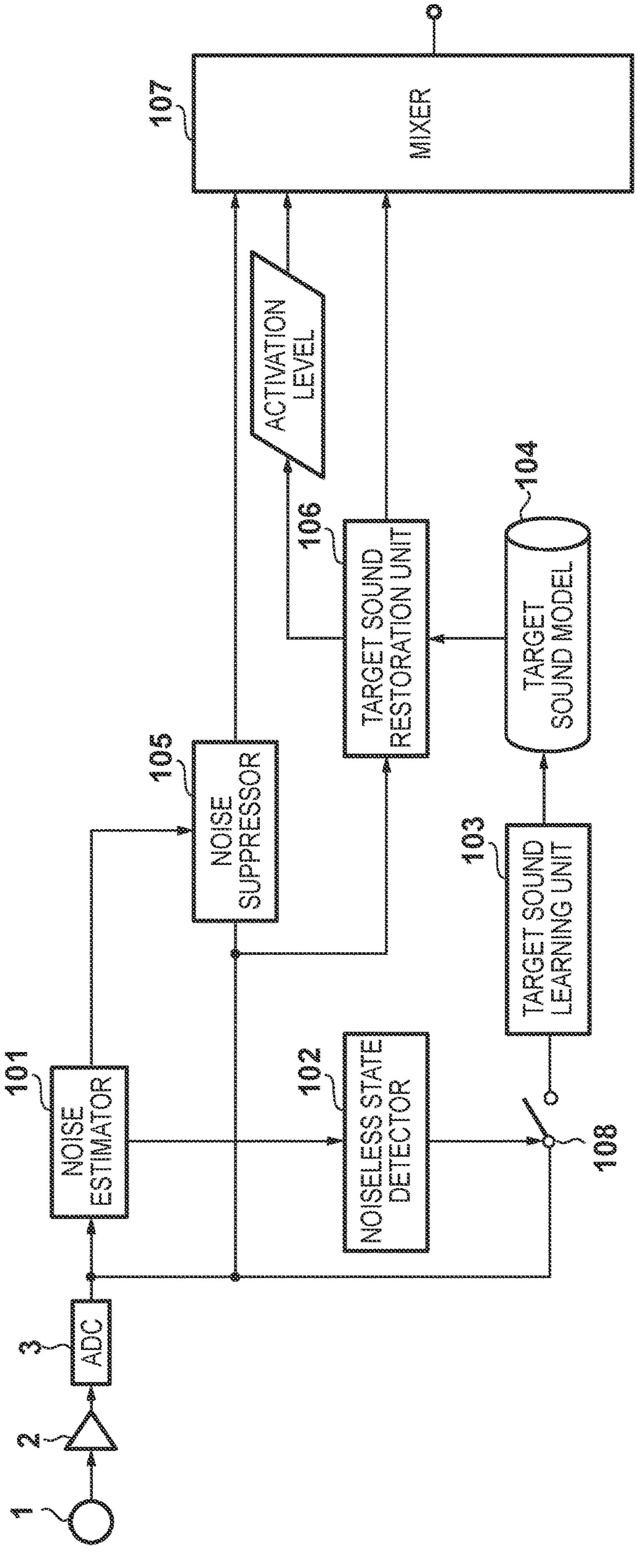
FIG. 1 is a block diagram showing a configuration of a sound capture apparatus according to Embodiment 1.

Hereinafter, embodiments of the present invention will be described in detail with reference to the drawings. It should be noted that the configurations described in the following embodiments are merely examples, and that the present invention is not limited to the configurations shown in the drawings.

Embodiment 1

FIG. 1 is a block diagram showing a configuration of a sound capture apparatus according to Embodiment 1.

In FIG. 1, reference numeral 1 denotes a microphone unit serving as a sound capture unit that captures ambient sounds containing a target sound, and converts the target sound into an electric signal. Numeral 2 denotes a microphone amplifier that amplifies a weak analog audio signal output by the microphone unit 1, and outputs the amplified signal. Numeral 3 denotes an analog-to-digital converter (ADC) that converts the input analog audio signal into a digital audio signal, and outputs the digital audio signal as a captured audio signal.

Numeral 101 denotes a noise estimator that estimates a non-stationary noise contained in the input captured audio signal, and outputs an estimated noise signal. Numeral 102 denotes a noiseless state detector that detects whether the estimated noise signal output by the noise estimator 101 is in a noiseless state (state in which there is weak noise, or no noise has occurred), and outputs a switch ON signal to a switch 108 only if the estimated noise signal is in the noiseless state. Expressed more quantitatively, the noiseless state means a state in which the noise level indicating the intensity of the noise is at or below a predetermined level that is not perceived as a noise.

Numeral 103 denotes a target sound learning unit that analyzes the input digital audio signal as a target sound signal, learns the characteristics thereof such as the spectral envelope and the harmonic structure, classifies these characteristics into a plurality of patterns, and outputs the patterns to a target sound model 104.

Numeral 104 denotes a target sound model that stores pattern information on the target sound signal output by the target sound learning unit 103, and supplies the pattern information to a target sound restoration unit 106 as needed. Numeral 105 denotes a noise suppressor that outputs a signal obtained by suppressing the estimated noise from the captured audio signal (noise-suppressed signal), according to the estimated noise signal output by the noise estimator 101. Numeral 106 denotes a target sound restoration unit that restores the target sound signal by performing pattern matching between the captured audio signal and the pattern information stored in the target sound model 104, and outputs the restored signal as a target sound restoration signal. The target sound restoration unit also outputs the activation level of the target sound pattern at this time.

Numeral 107 denotes a mixer that performs, as needed, replacement or mixing of the noise-suppressed signal output from the noise suppressor 105 and the target sound restoration signal output by the target sound restoration unit 106, according to the activation level of the target sound model, which is the learned model, and outputs the resulting signal. Here, the mixer 107 also functions as a signal selector that selects a signal to be processed from among a plurality of signals that are input.

Note that the sound capture apparatus may include, in addition to the above-described configuration, standard components (e.g., a CPU, a RAM, a ROM, a hard disk, an external storage device, a network interface, a display, a keyboard, a mouse, and the like) that are installed on a general-purpose computer. For example, the processing in various flowcharts described below can also be executed by a CPU reading out and executing a program stored in a hard disk or the like.

The following is a description, in accordance with the flow, of a series of operations of suppressing a non-stationary noise contained in a captured audio signal in the configuration of FIG. 1, while preventing loss of target sound components and deterioration in sound quality.

Figure 2:
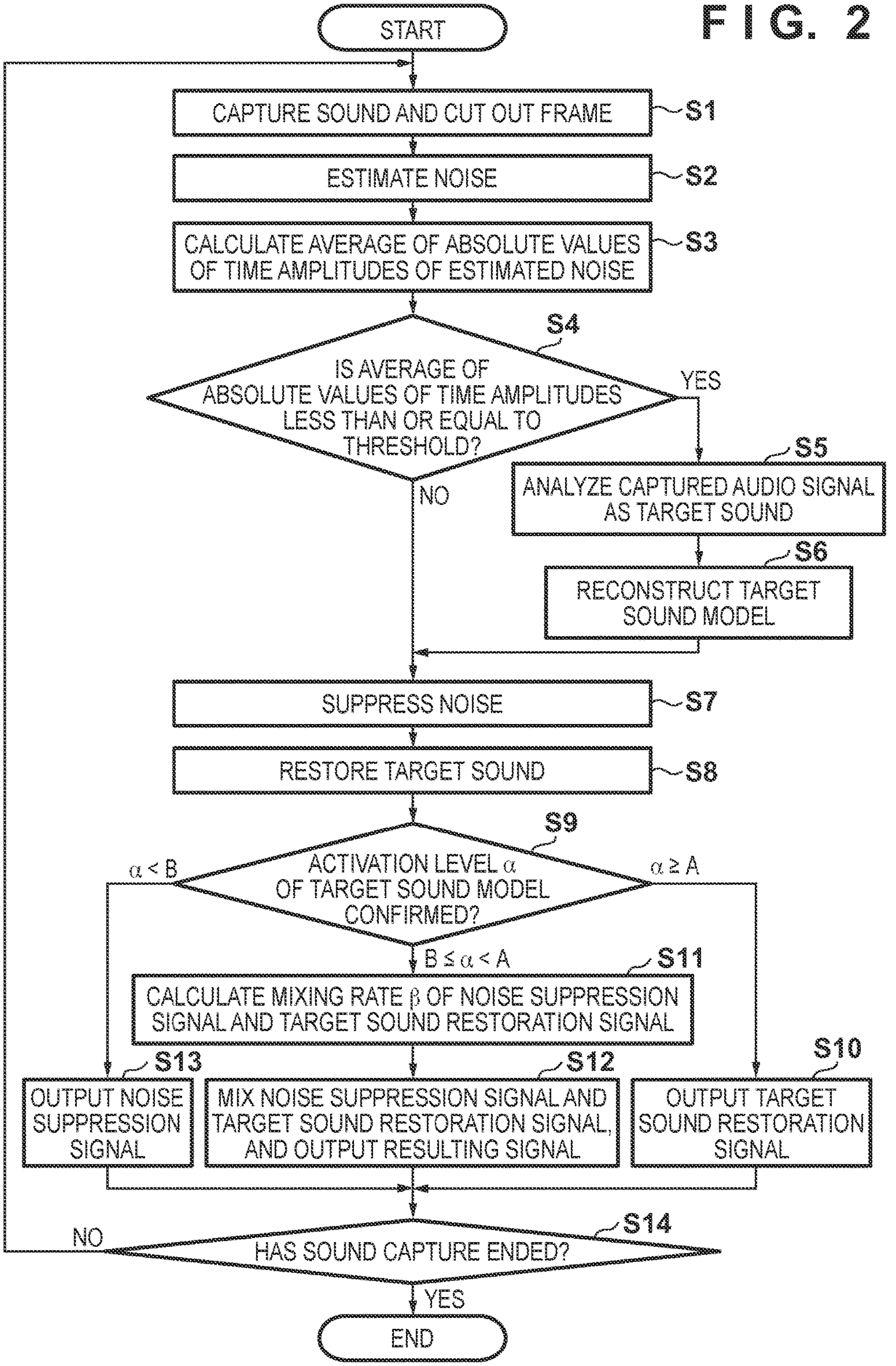
FIG. 2 is a flowchart illustrating sound capture processing performed by the sound capture apparatus according to Embodiment 1.

FIG. 2 is a flowchart illustrating sound capture processing performed by the sound capture apparatus according to Embodiment 1.

First, at step S1, ambient sounds containing the target sound are converted into an electric signal by the microphone unit 1, the electric signal is amplified by the microphone amplifier 2, and the amplified signal is converted into a digital signal in the ADC 3. A processing unit frame having a predetermined sample length is cut out from the digital signal, and is output.

At step S2, in the noise estimator 101, the noise signal contained in the processing frame of the captured audio signal that has been cut out at step S1 is estimated. In Embodiment 1, a method in which a component that was not be able to be predicted by using linear prediction is estimated as a non-stationary noise or a method in which a component that does not match a pre-learned sound source (sound) signal model is estimated as a non-stationary noise is used as the method for estimating a non-stationary noise from a monaural audio signal, for example. Note that these noise estimation processes are known and commonly used, and therefore, the detailed description thereof shall be omitted.

At step S3, in the noiseless state detector 102, an average (noise level) of the absolute values of time amplitudes of the estimated noise signal obtained at step S2 in the relevant processing frame is calculated. This can be calculated using the following equation (1).

$$\frac{\sum_{t=1}^{T} |a_t|}{T} \tag{1}$$

In the equation, T represents the number of frame samples, and $a_t$ represents the time amplitude of the estimated noise signal at time t within the frame.

At step S4, in the noiseless state detector 102, it is determined whether the average of the absolute values of time amplitudes calculated at step S3 is less than or equal to a predetermined threshold. If the average of the absolute values of time amplitudes is greater than the threshold (NO at step S4), the noiseless state detector 102 determines that the time interval of the processing frame is in a noise state, and proceeds to step S7. In this case, the noiseless state detector 102 outputs no signal.

On the other hand, if the average of the absolute values of time amplitudes is less than or equal to the threshold (YES at step S4), the noiseless state detector 102 determines that the time interval of the processing frame is in the noiseless state, and proceeds to step S5. In this case, the noiseless state detector 102 outputs a switch ON signal to the switch 108. Thereby, the switch 108 is connected, so that the captured audio signal is input into the target sound learning unit 103.

At step S5, in the target sound learning unit 103, the characteristic of the captured audio signal of the processing frame is analyzed as a target sound. This analysis provides the spectral envelope, the harmonic structure, the time waveform envelope, or the like of the captured audio signal as an analysis result.

At step S6, in the target sound learning unit 103, the target sound model 104 is reconstructed by adding the characteristic of the captured audio signal obtained at step S5 as a target sound model variable to the target sound model 104.

Through the processing described above, the captured audio signal of the processing frame that is determined to be in the noiseless state at step S4 is analyzed as the target sound signal at step S5, and the characteristic of the target sound signal is added as the target sound model variable at step S6, thereby reconstructing the target sound model 104. This makes it possible to learn a more accurate target sound model variable from the captured audio signal, while avoiding an influence of the non-stationary noise.

At step S7, in the noise suppressor 105, noise suppression is performed on the captured audio signal of the processing frame, based on the estimated noise signal obtained at step S2. In Embodiment 1, this processing is performed by subtracting the spectral amplitude of the estimated noise signal from the spectral amplitude of the captured audio signal.

Note that the use of spectral subtraction in Embodiment 1 is merely an example. For example, the same processing can also be effected by performing high-pass filter processing for which the cut-off frequency is defined based on the spectral energy distribution of the estimated noise signal. Alternatively, a Wiener filter may be designed by calculating the proportion of energy occupied by the estimated noise for each frequency component of the processing unit frame, and processing of removing estimated noise components from the captured audio signal may be performed. However, these are not intended to limit the scope of the present invention.

At step S8, in the target sound restoration unit 106, the characteristic of the captured audio signal is analyzed, and the target sound is restored by performing modeling using the target sound model variable stored in the target sound model 104. Specifically, pattern matching is performed between the characteristic obtained by analysis of the captured audio signal, such as the spectral envelope and the harmonic structure, and the target sound model variable stored in the target sound model 104. Next, the target sound signal is restored by modeling a captured audio signal by combining the matched patterns, and the restored sound signal is output.

For example, in Embodiment 1, an LPC (Linear Prediction Coding) spectral envelope, which is commonly used in the art, is used as the model variable of the spectral envelope. An LPC spectral envelope obtained by linear prediction analysis of the captured audio signal of the frame to be processed is represented by g(λ), and the i-th LPC spectral envelope stored in the target sound model 104 is represented by $f_i(\lambda)$. In Embodiment 1, matching between these two is calculated using a cosh scale. The cosh scale is calculated by the following equation (2).

$$\mathrm{COSH}_{fi} = \frac{1}{2\pi}\int_{-\pi}^{\pi} 2\cdot\{\cosh(\log f_i(\lambda) - \log g(\lambda)) - 1\}\,d\lambda \tag{2}$$

In the equation, λ represents the angular frequency (−π<λ≤π).

Here, the difference between the logarithm spectra of $f_i(\Delta)$ and g(Δ) is represented by V(Δ).

$$V(\lambda)=\log f_i(\lambda)-\log g(\lambda) \tag{3}$$

From the equation (2), the value of the $\mathrm{COSH}_{fi}$ can be described using V(λ) by the following equation (4).

$$\mathrm{COSH}_{fi} = \frac{1}{2\pi}\int_{-\pi}^{\pi} (e^{V(\lambda)} + e^{-V(\lambda)} - 2)\,d\lambda \tag{4}$$

The Taylor expansion of the integral term in the equation (4) about V(λ)=0 gives the following equation (5).

$$e^{V(\lambda)} + e^{-V(\lambda)} - 2 = \sum_{i=1}^{\infty} \frac{2}{(2i)!} V(\lambda)^{2i} = V(\lambda)^2 + \frac{1}{12}V(\lambda)^4 + \frac{1}{360}V(\lambda)^6 + \dots \tag{5}$$

Accordingly, if |V(λ)| is small, or in other words, if the degree of matching is high, the value of the $\mathrm{COSH}_{fi}$ has a weight that is very close to the square of that value. On the other hand, if |V(λ)| is large, or in other words, if the degree of matching is low, the value of the $\mathrm{COSH}_{fi}$ has a weight of an exponential function $e^{|V(\lambda)|}$.

As described above, the calculation using the equation (2) is performed for all of the LPC spectral envelopes stored in the target sound model 104, and the LPC spectral envelope f having the smallest COSH value is used as the model variable for use in the target sound restoration.

At this time, the activation level $\alpha_{spctr}$ of the selected LPC spectral envelope f is calculated by the following equation (6).

$$\alpha_{spctr} = \frac{1}{1 + \mathrm{COSH}_f} \tag{6}$$

The smaller the difference between the LPC spectral envelope referenced as the model variable and the LPC spectral envelope of the captured audio signal, the smaller the COSH value is and gets as close as possible to 0. Therefore, the higher the degree of matching with the model variable, the closer the value of $\alpha_{spctr}$ is to 1. In addition, the smaller the degree of matching, the larger the COSH value is, and thus the value of $\alpha_{spctr}$ gets close to 0.

Next, the target sound restoration unit 106 matches all of the harmonic structures stored in the target sound model 104 to the harmonic structure of the captured audio signal, and selects the best matching harmonic structure as the model variable used for the target sound restoration. Furthermore, the target sound restoration unit 106 calculates the activation level $\alpha_{harm}$ of that harmonic structure such that it has a similar range of values to that of $\alpha_{spctr}$.

Next, the target sound restoration unit 106 performs convolution of the spectral envelope and the harmonic structure that provide the largest activation level in the frequency domain, and the target sound restoration signal in the time domain is restored by performing inverse FFT.

At this time, the overall activation level α of the target sound model 104 is calculated by the following equation (7).

$$\alpha = \frac{\alpha_{spctr} + \alpha_{harm}}{2} \tag{7}$$

The target sound restoration unit 106 outputs the activation level α to the mixer 107, simultaneously with the target sound restoration signal.

At step S9, in the mixer 107, the value of the activation level α of the target sound model 104 calculated at step S8 is checked, and is compared with predetermined thresholds A and B. Note that A>B is satisfied.

Here, for example, various audibility comparison tests are performed for the target sound restoration signals restored under various a values and the actual target sound signal. The a values for which significance was observed with a significance level of 5% in the test results are used as the a values of the actual values of A and B. More specifically, A is the smallest value among the a values where significance was observed with a significance level of 5% for the fact that the target sound restoration signal and the target sound signal are substantially equal. On the other hand, B is the largest value among the a values where significance was observed with a significance level of 5% for the fact that the target sound restoration signal and the target sound signal are completely different.

As a result of comparison at step S9, if $\alpha \geq A$ is satisfied, it is determined in the mixer 107 that the target sound restoration signal obtained at step S8 is substantially equal to the actual target sound. Then, at step S10, in the mixer 107, the target sound restoration signal input from the target sound restoration unit 106 is directly output (first output mode).

As a result of comparison at step S9, if $B \leq \alpha < A$ is satisfied, it is determined in the mixer 107 that the target sound restoration signal obtained at step S8 contains the actual target sound to a certain degree. Then, at step S11, the mixing rate (3 of the noise suppression signal and the target sound restoration signal is calculated in the mixer 107. This is calculated by the following equation (8), for example, based on the activation level $\alpha$ of the target sound model 104.

$$\beta=(A-\alpha)/(A-B) \tag{8}$$

At step S12, the noise suppression signal and the target sound restoration signal are mixed based on the mixing rate $\beta$ calculated at step S11, and the resulting signal is output (second output mode). When the time amplitude of the noise suppression signal for a given time t is represented by $z_t$, the time amplitude of the target sound restoration signal is represented by $s_t$, the mixed signal $m_t$ for the time t is calculated by the following equation (9).

$$m_t=\beta \cdot z_t+(1-\beta) \cdot s_t \tag{9}$$

According to the equation (8), the larger the activation level $\alpha$, the smaller the mixing rate $\beta$ is. Therefore, the proportion of the target sound restoration signal in the mixed signal is larger according to the equation (9).

Note that although mixing is performed in the time domain in Embodiment 1, mixing may be performed in the frequency domain.

As a result of comparison at step S9, if $\alpha < B$ is satisfied, it is determined in the mixer 107 that the target sound restoration signal obtained at step S8 contains substantially no actual target sound. Then, at step S13, in the mixer 107, the noise suppression signal generated at step S7 is output (third output mode). Doing so makes it possible to prevent an erroneously restored signal from being reflected in the final output when the learned model is not activated.

By performing the processing from steps S9 to S13, it is possible to determine the likelihood of the target sound restoration signal according to the activation level $\alpha$ of the learned target sound model, thereby deciding which of the replacement output mode and the mixing output mode of the target sound restoration signal and the noise suppression signal is to be used. This can prevent entry of an incomplete target sound restoration signal resulting from an incomplete learned model, while supplementing the target sound component lost by the noise, and it is therefore possible to extract a more accurate target sound signal.

At step S14, it is determined whether there is an instruction from a control unit (not shown) to end the sound capture processing. If there is no instruction (NO at step S14), the process returns to step S1. On the other hand, if there is an instruction (YES at step S14), the sound capture processing ends.

As described above, according to Embodiment 1, the characteristic of the target sound is learned from the input signal during a noiseless interval, and the target sound component lost by noise suppression is restored with the learned model. Additionally, the noise suppression signal is corrected according to the learned model and the activation level of the learned model by the input signal. This makes it possible to prevent tone alteration and loss of target sound components, while suppressing the wind noise.

More specifically, by using the non-stationary nature of a noise, the characteristic of the target sound is learned in an interval in which there is weak noise or no noise has occurred (noiseless interval), and the signal correction after noise suppression is controlled according to the state of matching between the learned model and the input signal. Accordingly, even in the case of a target sound signal having no harmonicity, the target sound signal lost by noise suppression processing can be restored by a learned model, and a signal having undergone wind noise suppression can be more precisely corrected.

Embodiment 2

In Embodiment 2, a description will be given of a configuration in which a plurality of signals are input and NMF (Nonnegative Matrix Factorization) is used as the method of leaning the target sound.

Figure 3:
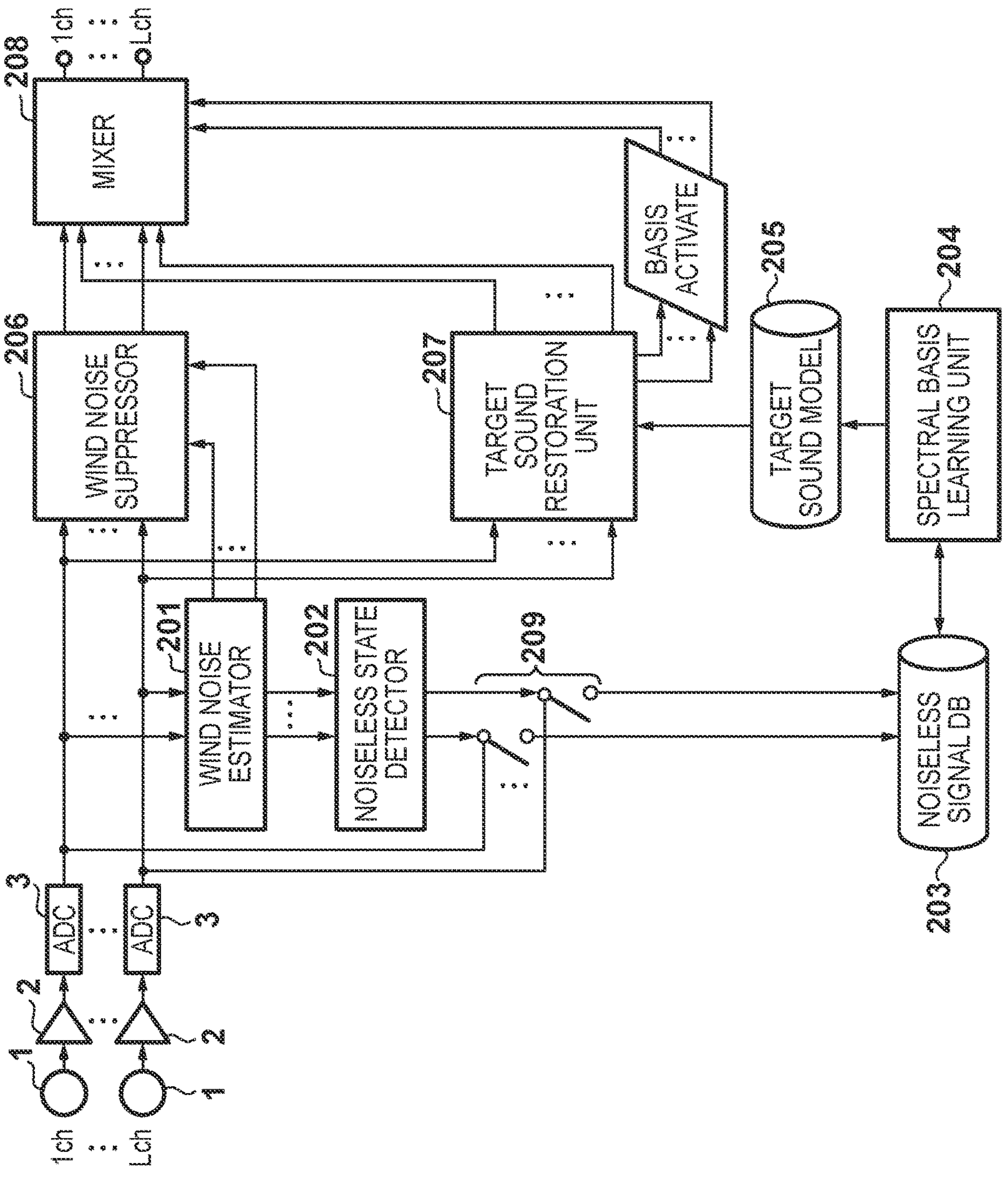
FIG. 3 is a block diagram showing a configuration of a sound capture apparatus according to Embodiment 2.

FIG. 3 is a block diagram showing a sound capture apparatus according to Embodiment 2.

The microphone unit 1, the microphone amplifier 2, and the ADC 3 in FIG. 3 are the same as those of the configuration shown in FIG. 1, and therefore, the description thereof shall be omitted. In the configuration of Embodiment 2, each of the microphone unit 1, the microphone amplifier 2, and the ADC 3 is provided for L channels (L is a natural number) from 1ch to Lch, and audio signals of L channels are captured. L microphone units 1 may be directed in various directions, including, up, down, left, right, front, and back on the same spherical plane, or may all be directed in parallel in the same direction on the same plane or a line.

Numeral 201 denotes a wind noise estimator that estimates, from the captured audio signals of L channels, the wind noise signal of each of the channels, and outputs an estimated noise signal. Numeral 202 denotes a noiseless state detector that determines whether each of the estimated noise signals of L channels is in the noiseless state, and outputs switch ON signals for the channels determined to be in the noiseless state to the respective switches 209. Numeral 203 denotes a noiseless signal DB (database) that stores and saves the input signal of each of the channels in the relevant frame that are determined to be in the noiseless state.

Numeral 204 denotes a spectral basis learning unit that learns the input signals stored in the noiseless signal DB 203 by using NMF. Numeral 205 denotes a target sound model that stores a spectral basis that is output as a result of learning the target sound in the spectral basis learning unit 204, and outputs the spectral basis as needed. Numeral 206 denotes a wind noise suppressor that performs wind noise suppression processing on the captured audio signals of L channels, based on the estimated noise signals of L channels output by the wind noise estimator 201, and outputs a noise-suppressed signal.

Numeral 207 denotes a target sound restoration unit that performs restricted NMF on the captured audio signals of L channels by using the spectral basis stored in the target sound model 205, calculates basis activates for L channels to restore the target sound signals for L channels that are contained in the captured audio signals, and outputs the restored signals as the target sound restoration signals. Numeral 208 denotes a mixer that selects or mixes the noise-suppressed signals for L channels output from the wind noise suppressor 206 and the target sound restoration signals for L channels that are output from the target sound restoration unit 207 for each channel, and outputs the resulting signals. Note that the decision as to whether to perform selection or mixing is made based on the magnitude of the coefficient of the basis activates for L channels that are output from the target sound restoration unit 207.

The following is a description, in accordance with the flow, of a series of operations of correcting the target sound that is lost by noise suppression based on a model learned by NMF in the configuration shown in FIG. 3, while suppressing the non-stationary noise (wind noise) contained in a captured audio signal.

Figure 4A:
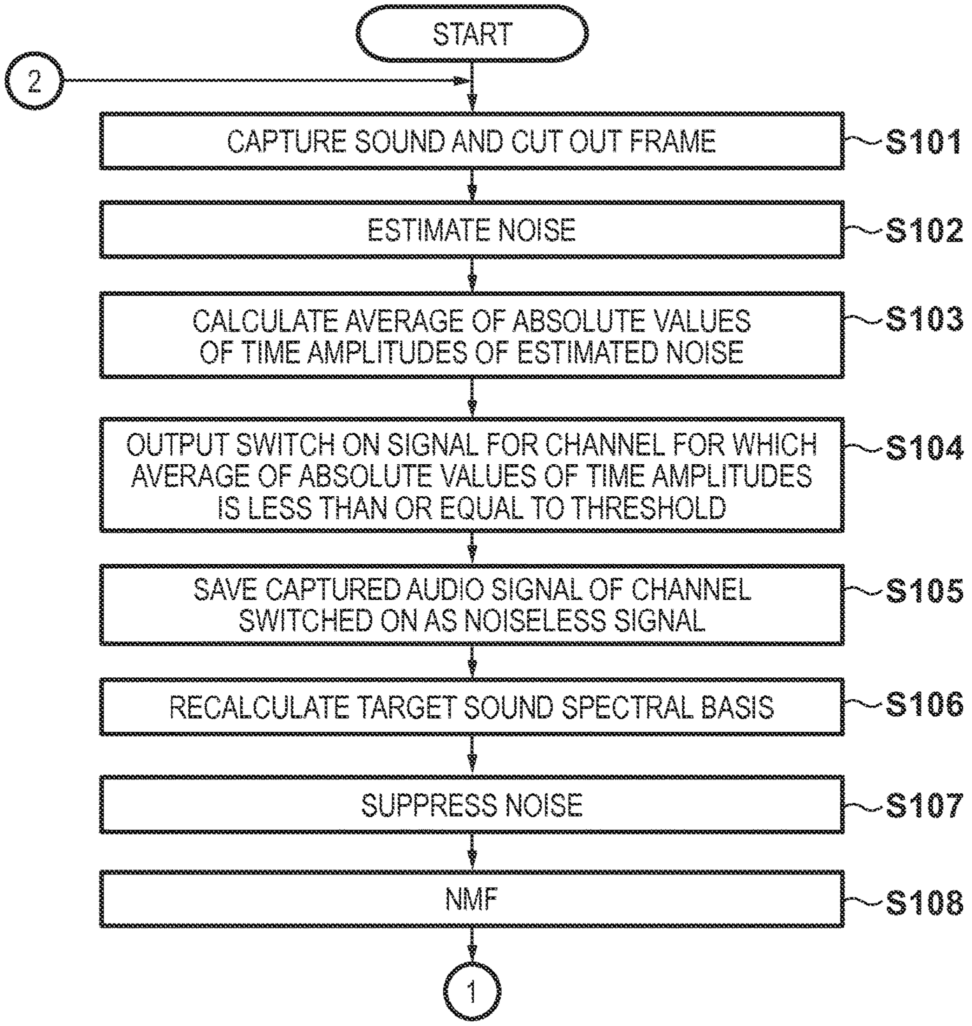
FIGS. 4A and 4B are flowcharts illustrating sound capture processing performed by the sound capture apparatus according to Embodiment 2.
Figure 4B:
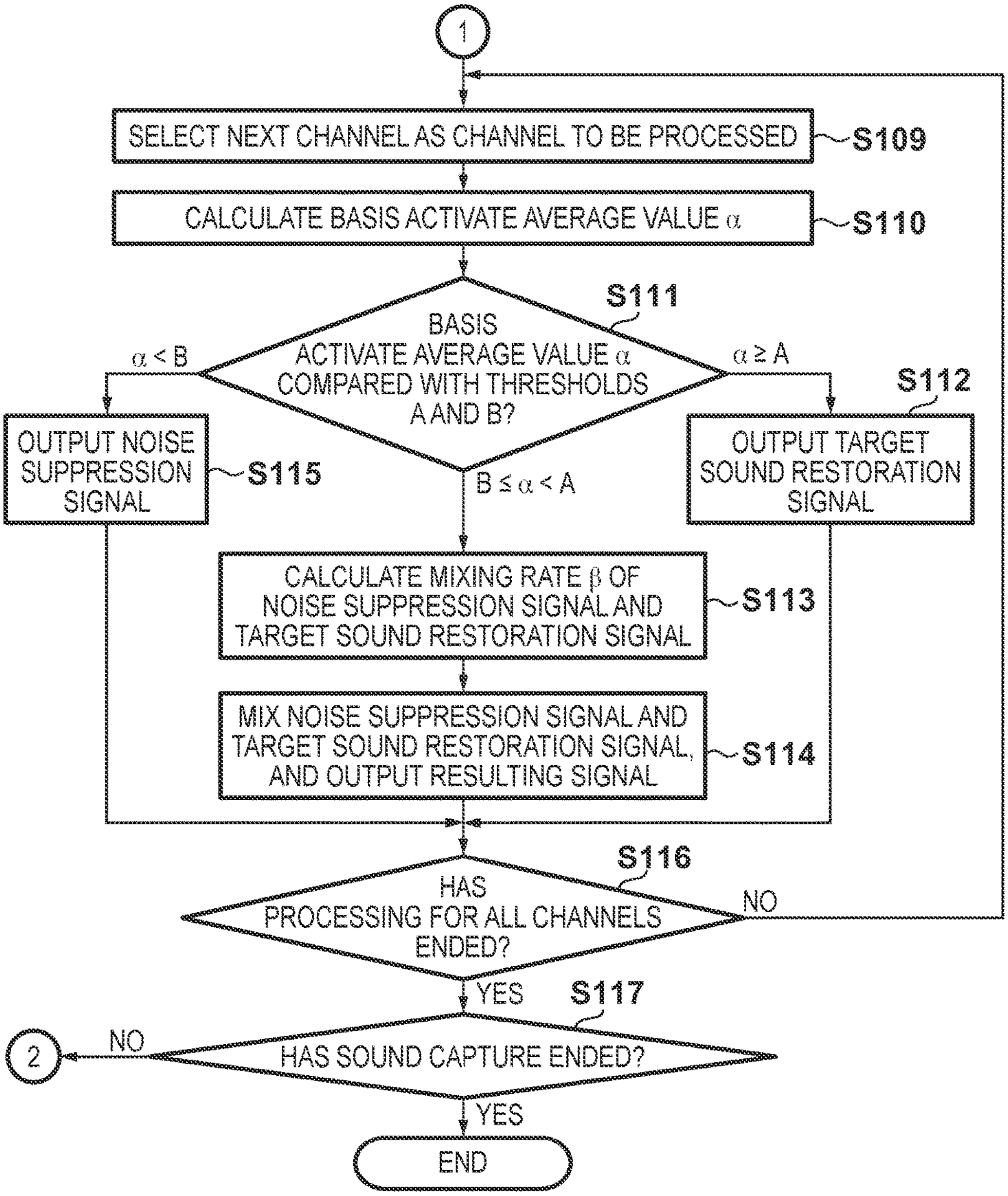

FIGS. 4A and 4B are flowcharts illustrating sound capture processing performed by the sound capture apparatus according to Embodiment 2.

First, at step S101, ambient sounds are captured and converted into an electric signal in the microphone unit 1, the electric signal is amplified by the microphone amplifier 2, the amplified signal is converted into a digital signal in the ADC 3, and the digital signal is cut out into a processing unit frame having a predetermined sample length, and is output. At step S101, this processing is performed in parallel for L channels.

At step S102, in the wind noise estimator 201, the captured audio signals for L channels that have been cut out at step S1 are analyzed, and the wind noise contained therein is estimated. Examples of the method for estimating a diffusive noise such as a wind noise from multichannel captured audio signals include the following: a method that extracts a non-directional noise by using a beam former to direct a null in the direction in which a directional component, or in other words, a target sound arrives; and a method that extracts only a diffusive signal by using ICA (independent component analysis). Since the wind noise and the target sound are completely different in diffusivity and directivity in a space, the use of these methods can effectively estimate the wind noise.

Depending on the technique, the estimated noise signals estimated by these methods may be all integrated into a monophonic signal for L channels, and be output. However, by performing the inverse transform of multichannel processing during estimation on the estimated noise signals, the estimated noise signals can be converted into signals for L channels. In Embodiment 2, the estimated noise signals for L channels corresponding to the channels of the captured audio signals are obtained by step S102. These methods are commonly used as source separation techniques and known, and therefore, the detailed description thereof shall be omitted.

At step S103, in the noiseless state detector 202, an average of the absolute values of time amplitudes is calculated for each of the estimated noise signals for L channels that have been estimated at step S102. This calculation is performed by the equation (1) as with step S3 shown in FIG. 2.

At step S104, in the noiseless state detector 202, whether the average of the absolute values of time amplitudes of each of the channels that has been calculated at step S103 is less than or equal to the predetermined threshold, and switch ON signals of the channels for which the average is less than or equal to the threshold are output to the respective switches 209. By this processing, the switches 209 that connect the noiseless signal DB 203 and the captured audio signals of the channels for which the switch ON signals have been output are turned ON.

At step S105, in the noiseless signal DB 203, each of the captured audio signals of the channels for which the switch ON signals have been output by step S104 is saved as a noiseless signal.

At step S106, in the spectral basis learning unit 204, learning using NMF is performed based on the noiseless signal DB 203 updated by step S105. Specifically, this learning is performed as follows.

First, short-time Fourier transform is performed on each of the captured audio signals newly stored in the noiseless signal DE 203 to create a spectrogram, and the spectrogram is added to the end of the spectrograms created by the past frame processing. This spectrogram is represented by a two-dimensional matrix V having a size of M×N. Here, M represents the resolution of the spectrum, and N represents the time sample of the spectrogram. Next, this is decomposed into K base spectra and their respective activation levels. That is, the spectrogram is decomposed into a product of a nonnegative spectral basis matrix H of M×K and a nonnegative basis activate U of K×N.

$$V \cong HU \tag{10}$$

Here, the cost function is as expressed in the following equation (11).

$$\|V-HU\|_F^2=\Sigma_{m,n}|V_{m,n}-\Sigma_k H_{m,k}U_{k,n}|^2 \tag{11}$$

The equation (11) is called a Frobenius norm.

In Embodiment 2, learning is performed by optimizing the spectral basis and the basis activate such that the value of the equation (11) becomes minimum. As a general solution to the Frobenius norm, an auxiliary function is created using Jensen's inequality, and substituting an equation that optimizes the auxiliary function gives the following optimizing equations.

$$H_{m,k} \leftarrow H_{m,k}\frac{\Sigma_n V_{m,n}U_{k,n}}{\Sigma_n U_{k,n}\Sigma_{k'} H_{m,k'}U_{k',n}} \tag{12}$$

$$U_{k,n} \leftarrow U_{k,n}\frac{\Sigma_n V_{m,n}H_{m,k}}{\Sigma_n H_{m,k}\Sigma_{k'} H_{m,k'}U_{k',n}} \tag{13}$$

By repeating the update of the spectral basis and the basis activate by the equations (12) and (13) until the values converge, optimization, or in other words, learning of the target sound model variable is performed.

As a result of this processing, the target sound spectral basis matrix H updated as described above is output to the target sound model 205. Additionally, the spectrogram, the spectral basis matrix H, and the basis activate matrix U that have been created are stored in the noiseless signal DB 203 in order to be used as the initial values for NMF processing in the next frame. By doing so, the spectral basis matrix H can be learned so as to be more faithful to the target sound signal as the number of the noiseless signals saved in the noiseless signal DB 203 increases.

At step S107, in the wind noise suppressor 206, wind noise suppression on the captured audio signal is performed for each channel. This is performed for each channel by using the same technique as with step S7 in FIG. 2.

At step S108, in the target sound restoration unit 207, the spectral basis stored in the target sound model 205 is optimized without being changed. First, the captured audio signal of each of the channels is converted into a spectrogram matrix $V_{ch}$ of M×T. Here, T represents the number of time samples of the captured audio signal of the processing frame. Next, using a calculating equation obtained by replacing V with $V_{Ch}$ and n with t in the equation (13), only the basis activate is repeatedly calculated until the value converges.

Thus, the basis activate matrix $U_{ch}$ having a size K×T for the captured audio signal of each of the channels is calculated. Likewise, using the calculated basis activate and spectral basis, a target sound restoration signal $S_{ch}$ of each of the channels is generated. This is calculated by the following equation (14).

$$S_{ch}=HU_{ch} \tag{14}$$

The basis activate and the target sound restoration signal are output to the mixer 208.

The individual processing from steps S109 to S116 is repeatedly performed for all of the channels of the captured audio signals.

At step S109, the next channel to be processed is selected in the mixer 208. The channel to be processed is selected in order from 1ch to Lch of the captured audio signals.

At step S110, a basis activate average value α (the magnitude of the coefficient) of the entire processing frames of the basis activate calculated at step S108 is calculated for the captured audio signal corresponding to the channel to be processed.

When the amplitude of the basis activate at the t-th time sample of the spectral basis k is represented by $A_{k,t}$, and the number of base spectra is represented by K, and the number of time samples in the frame is represented by T, the basis activate average value α is calculated by the following equation (15).

$$\alpha = \frac{\sum_{k=1}^{K}\sum_{t=1}^{T}|A_{k,t}|}{K\cdot T} \tag{15}$$

At step S111, in the mixer 208, the basis activate average value α of the target sound model variable calculated at step S110 is checked, and is compared with the predetermined thresholds A and B. Note that A>B is satisfied.

As a result of comparison at step S111, if α≥A is satisfied, it is determined in the mixer 208 that the target sound restoration signal obtained at step S108 is substantially equal to the actual target sound, and the process proceeds to step S112.

As a result of comparison at step S111, if B≤α<A is satisfied, it is determined in the mixer 208 that the target sound restoration signal obtained at step S108 contains the actual target sound to a certain degree, and the process proceeds to step S113.

As a result of comparison at step S111, if α<B is satisfied, it is determined in the mixer 208 that the target sound restoration signal obtained at step S108 contains substantially no actual target sound, and the process proceeds to step S115.

The processing from steps S112 to S115 is the same as the processing from steps S10 to S13 shown in FIG. 2 in Embodiment 1, and therefore, the description thereof shall be omitted. After these processes end, the process proceeds to step S116.

At step S116, it is determined whether signal selection/mixing processing has ended for all of the channels. If the processing has not ended for all of the channels (NO at step S116), the process returns to step S109. On the other hand, if the processing has ended for all of the channels (YES at step S116), the process proceeds to step S117.

By performing the processing from steps S109 to S116, it is possible to determine the likelihood of the target sound restoration signal for each channel of the captured audio signal according to the activation level of the spectral basis, thereby deciding whether to select or to mix the target sound restoration signal and the noise suppression signal. Doing so makes it possible to prevent entry of an incomplete target sound restoration signal resulting from an incomplete learned model, while supplementing the target sound component lost by the noise, and it is therefore possible to extract a more accurate target sound signal.

At step S117, it is determined whether there is an instruction from a control unit (not shown) to end the sound capture processing. If there is no instruction (NO at step S117), the process returns to step S101. On the other hand, if there is an instruction (YES at step S117), the sound capture processing ends.

As described above, according to Embodiment 2, the characteristic of the target sound is learned from an input signal during a noiseless interval, and the target sound component that is lost by the noise suppression is restored by the learned target sound model. Additionally, the noise suppression signal is corrected according to the target sound model and the activation level of the target sound model by the input signal. This makes it possible to prevent tone alteration and loss of target sound components, while suppressing the wind noise.

Although in Embodiment 2, each of the estimated noise signals for which the average of the absolute values of time amplitudes of each of the channels is less than or equal to the predetermined threshold is determined as a noiseless signal at step S104 in FIG. 4A, this determination may be made based on other noise properties. For example, the wind noise is caused by a phenomenon that occurs independently in each microphone unit, therefore has no correlation between channels. Making use of this property, the correlation between the channels may be examined, and, if any one correlation of a channel with another channel has a degree greater than a predetermined threshold, the estimated noise signal of that channel can be determined as a noiseless signal.

Embodiment 3

In Embodiment 3, a description will be given of a configuration that performs matching using the high band of a spectral basis as a key in the case of restoring a target sound by NMF, thereby suppressing the influence of the wind noise during matching, while suppressing the throughput. In Embodiment 3, a description will be also given of a case where a more accurate target sound is obtained by correcting only the low band, which is influenced by the wind noise.

Figure 5A:
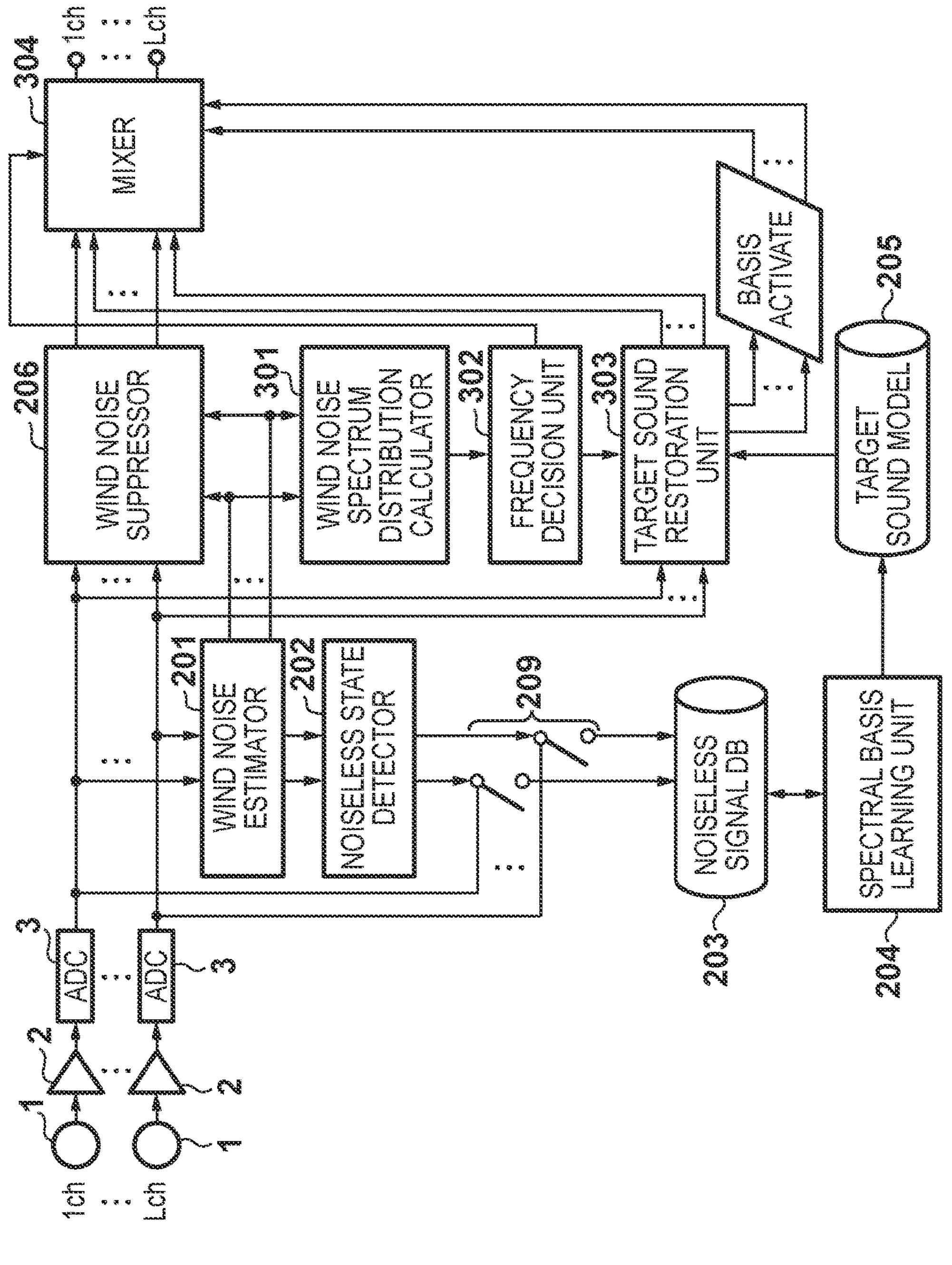
FIGS. 5A and 5B are block diagrams showing a configuration of a sound capture apparatus according to Embodiment 3.

FIG. 5A is a block diagram showing a configuration of a sound capture apparatus according to Embodiment 3.

In FIG. 5A, the components denoted by numerals 1 to 3, and 201 to 206 are the same as those shown FIG. 3 in Embodiment 2, and therefore, the description thereof shall be omitted.

Numeral 301 denotes a wind noise spectrum distribution calculator that converts the estimated noise signals for L channels output by the wind noise estimator 201 into frequency components for each channel. Then, the wind noise spectrum distribution calculator 301 calculates the spectral distribution of the entire estimated noise signals for L channels by determining a channel average of the frequency components, and outputs the spectral distribution.

Numeral 302 denotes a frequency decision unit that decides the frequency at which a captured audio signal is divided into a low band and a high band, based on the spectral distribution output by the wind noise spectrum distribution calculator 301. Here, the spectral energy of the wind noise is localized in the low band. Accordingly, the frequency decision unit 302 searches for a frequency around which the spectral energy is abruptly attenuated from the low band toward the high band and above which a large energy is not present, and outputs that frequency as a division frequency.

Numeral 303 denotes a target sound restoration unit that performs NMF processing on each of the channel signals of the captured audio signals for L channels by using a spectral basis above the division frequency, and calculates a basis activate for each of the channels. In addition, the target sound restoration unit 303 generates a target sound low-band restoration signal by using the calculate basis activate and low-band spectral basis, and output the signal. Note that the detailed configuration of the target sound restoration unit 303 will be described later with reference to FIG. 5B.

Numeral 304 denotes a mixer that mixes/selects low-band components of the noise-suppressed signals for L channels output from the wind noise suppressor 206 and the target sound low-band restoration signals (the target sound restoration signals of the low-band components) for L channels output from the target sound restoration unit 303, for each channel, and outputs resulting signals. Note that whether to perform selection or mixing is determined based on the division frequency output from the frequency decision unit 302.

Figure 5B:
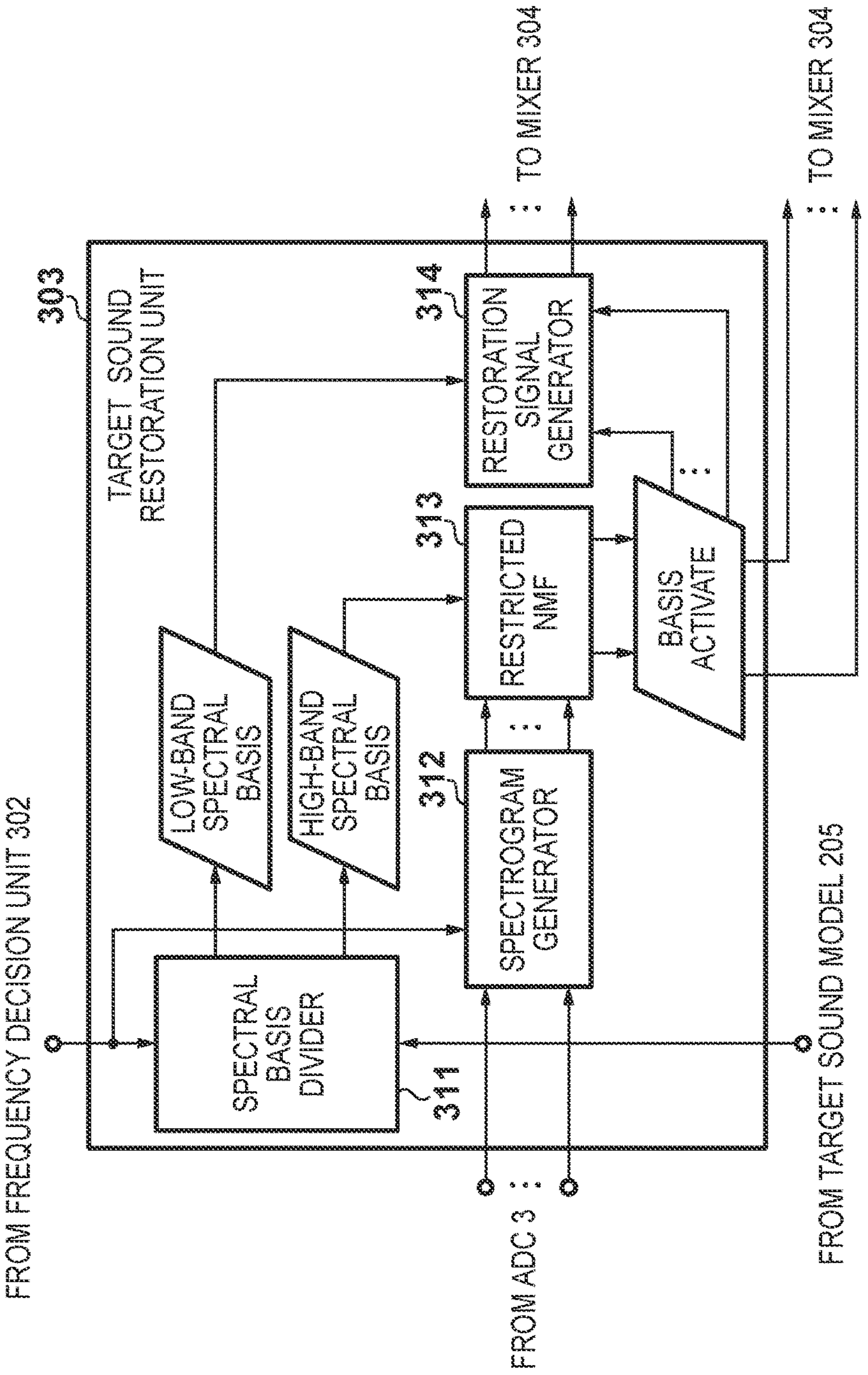

FIG. 5B is a block diagram showing the detailed configuration of the target sound restoration unit 303.

In FIG. 5B, numeral 311 denotes a spectral basis divider that divides the spectral basis stored in the target sound model 205 into a low band and a high band, according to the division frequency output by the frequency decision unit 302, and outputs the resultant.

Numeral 312 denotes a spectrogram generator that performs short-time Fourier transform on each of the channel signals of the captured audio signals for L channels, thereby generating a spectrogram serving as time-frequency information. Furthermore, the spectrogram generator 312 extracts high-frequency components above the division frequency that are not affected by the noise in the captured audio signals, based on the division frequency output by the frequency decision unit 302, and outputs the high-frequency components.

Numeral 313 denotes restricted NMF. The basis activates for L channels are calculated by decomposing the high-band components of the captured audio signals for L channels by NMF without changing the high-band spectral basis output by the spectral basis divider 311.

Numeral 314 denotes a restoration signal generator that generates target sound low-band restoration signals for L channels by taking the product of the low-band spectral basis output by the spectral basis divider 311 and the matrix of the basis activate for L channels output by the restricted NMF 313, and outputs the signals.

The following is a description, in accordance with the flow, of a series of operations of more accurately correcting a signal that has been subjected to wind noise suppression in the configuration shown in FIG. 5 by accurately restoring the target sound signal by calculating the basis activate in the high band that is not affected by the noise, and correcting the low band of the target sound signal that is affected by the noise by restoring it using the basis activate during the target sound restoration by NMF.

Figure 6A:
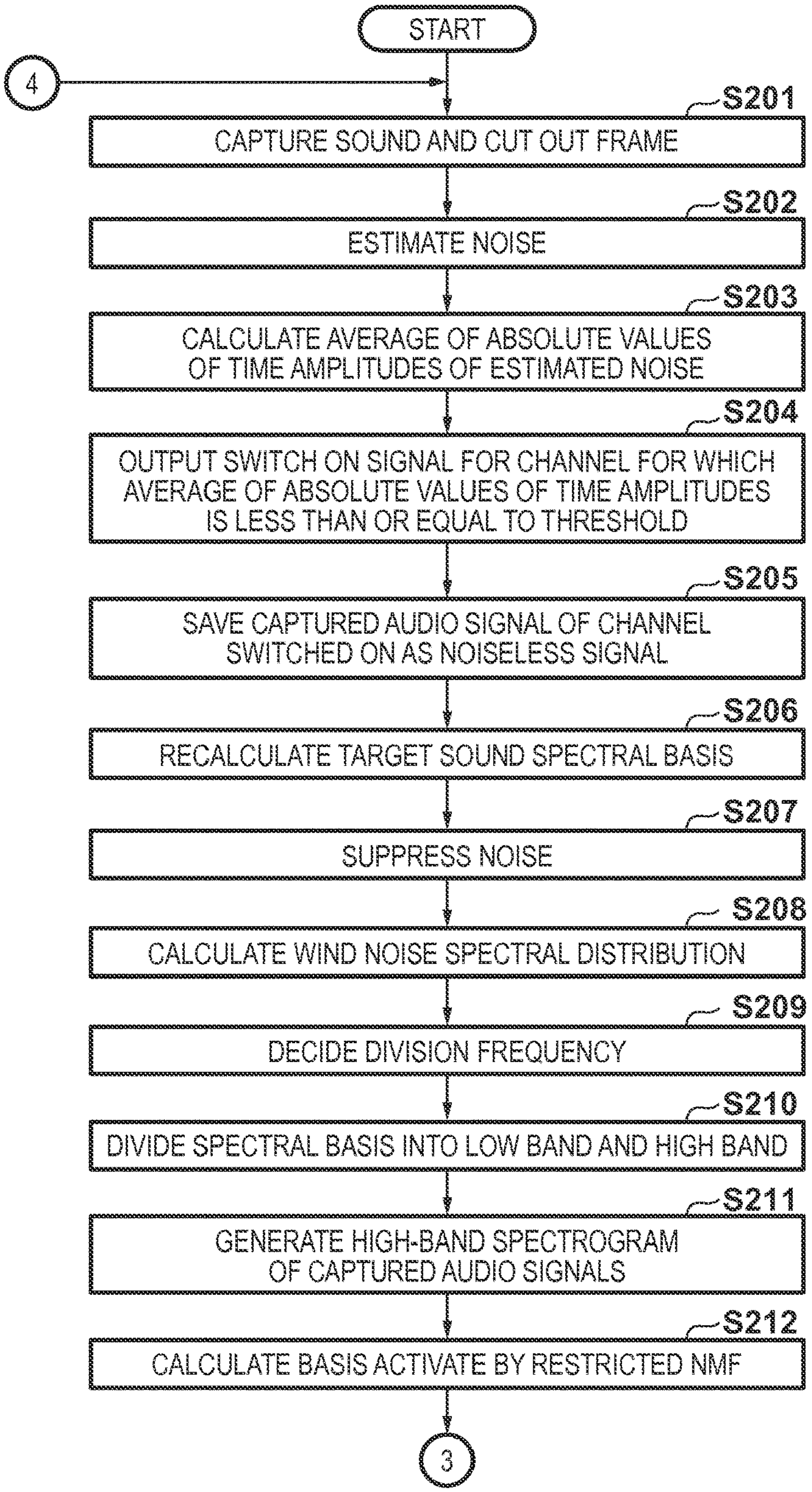
FIGS. 6A and 6B are flowcharts illustrating sound capture processing performed by the sound capture apparatus according to Embodiment 3.
Figure 6B:
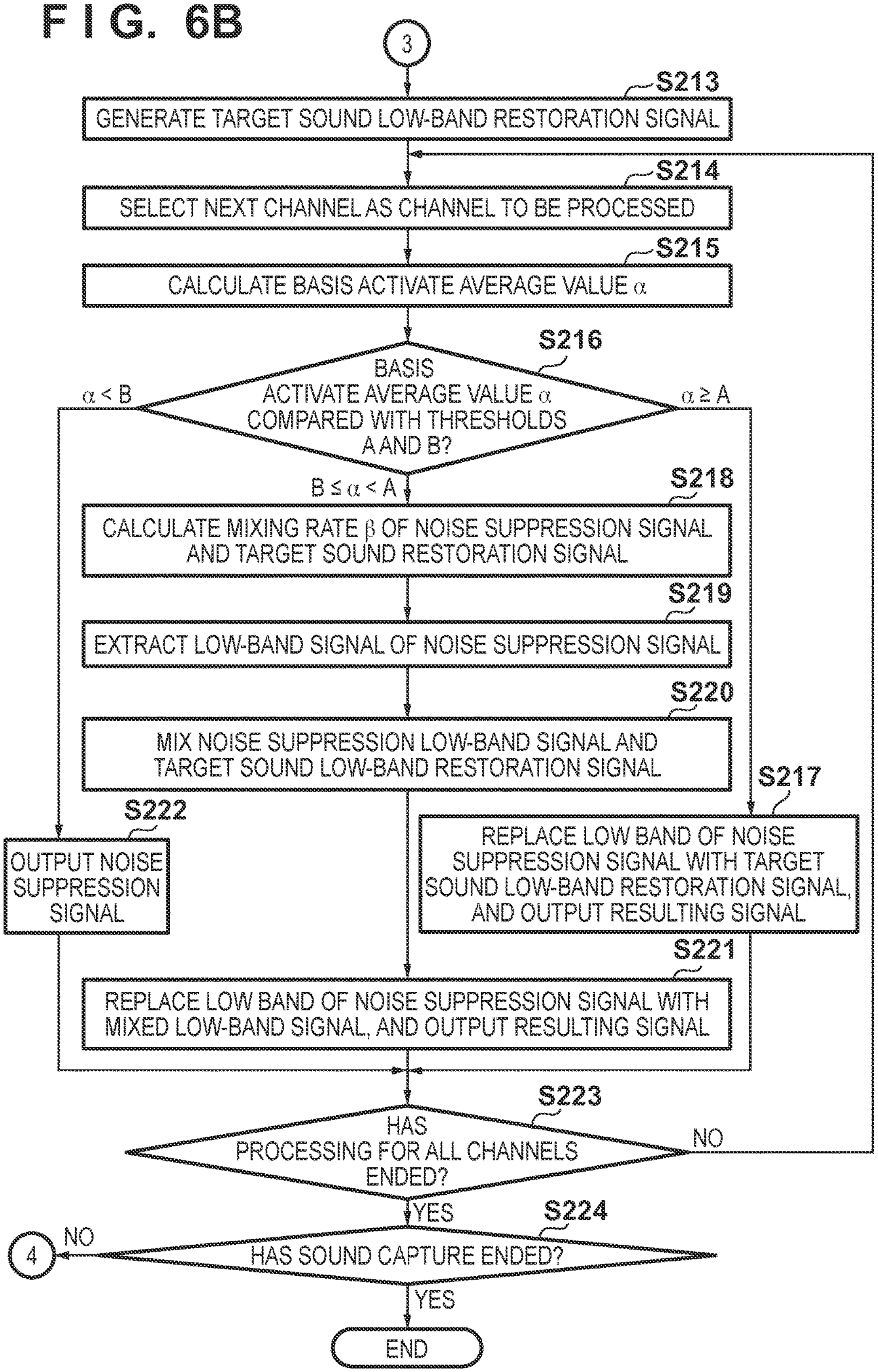

FIGS. 6A and 6B are a flowchart illustrating sound capture processing performed by the sound capture apparatus according to Embodiment 3.

The processing from steps S201 to S207 is the same as the processing from steps S101 to S107 in FIG. 4A of Embodiment 2, and therefore, the description thereof shall be omitted.

At step S208, in the wind noise spectrum distribution calculator 301, time-frequency conversion processing (e.g., FFT) is performed on the estimated noise signals for L channels output by the wind noise estimator 201 for each channel to convert them into frequency components. Next, in the wind noise spectrum distribution calculator 301, the spectral distribution of the entire estimated noise signals for L channels is calculated by determining a channel average of the absolute values of amplitudes of the frequency components, and is output. This processing is known in the art, and shall not be described in detail here.

At step S209, in the frequency decision unit 302, the wind noise spectral distribution calculated at step S208 is analyzed to decide a division frequency at which a low frequency band in which a majority of the wind noise components is concentrated and a high frequency band in which few wind noise components are present. For example, a frequency serving as a changing point where there is an abrupt attenuation in amplitude is searched for in the wind noise spectral distribution, and the lowest frequency at which an average of all frequency amplitudes above the changing point has a dB difference less than or equal to a predetermined threshold with respect to the peak amplitude is used as the division frequency.

At step S210, in the spectral basis divider 311, the spectral basis stored in the target sound model 205 is divided into a low band and a high band based on the division frequency decided at step S209. The spectral basis in Embodiment 3 is represented by a matrix. In this matrix, the rows represent specific frequency components, which are sorted in the order of frequencies. On the other hand, the columns represent individual base spectra. Thus, this division is made by horizontally dividing the matrix at the portion constituting the row around the division frequency.

At step S211, in the spectrogram generator 312, a high-band spectrogram of the captured audio signals for L channels is generated. The details of this processing have been previously described in the description of the spectrogram generator 312, and shall not be described here.

At step S212, in the restricted NMF 313, the basis activates for L channels are calculated by decomposing the high-band spectrograms for L channels generated at step S211 by NMF using the high-band spectral basis divided at step S210.

At step S213, in the restoration signal generator 314, the target sound low-band restoration signals for L channels are generated by calculating the product of the low-band spectral basis divided at step S210 and the matrix of the basis activates for L channels calculated at step S212.

The individual processing from steps S214 to S223 is repeatedly performed all of the channels of the captured audio signals of L channels, as in FIGS. 4A and 4B of Embodiment 2.

The processing from steps S214 to S216 is the same as the processing from steps S109 to S111 in FIG. 4B of Embodiment 2, and therefore, the description thereof shall be omitted.

At step S217, in the mixer 304, the low-band components of the noise suppression signals for L channels generated at step S207 are replaced with the target sound low-band restoration signals for the corresponding channels generated at step S213, based on the division frequency output by the frequency decision unit 302.

The processing of step S218 is the same as the processing at step S113 in FIG. 4B of Embodiment 2, and therefore, the description thereof shall be omitted.

At step S219, in the mixer 304, for each of the channels of the noise suppression signals for L channels generated at step S207, a low-band component below the division frequency is extracted.

At step S220, in the mixer 304, the low-band component of the noise suppression signal extracted at step S219 and the target sound low-band restoration signal generated at step S213 are mixed at the mixing rate calculated at step S218.

At step S221, in the mixer 304, the low-band component of the noise suppression signal is replaced with the mixed signal generated at step S220. This enables the target sound low-band restoration signal to be reflected in the noise suppression signal according to the basis activate, and it is therefore possible to perform more accurate correction.

The processing from steps S222 to S224 is the same as the processing from steps S115 to S117 in FIG. 4B of Embodiment 2, and therefore, the description thereof shall be omitted.

As described above, according to Embodiment 3, the basis activate is accurately calculated by decomposing the high-band captured audio signal, which is not affected by the noise, during the target sound restoration processing by NMF. Furthermore, the low band of the target sound signal is restored with the low-band spectral basis. Thereby, it is possible to more accurately restore a signal that has been subjected to the wind noise suppression.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-237350, filed Nov. 15, 2013, which is hereby incorporated by reference herein in its entirety.

What is claimed is:

1. An apparatus comprising:
a hardware processor; and
a memory which stores instructions to be executed by the hardware processor, wherein in accordance with the instructions executed by the hardware processor, the apparatus performs:
obtaining a first captured audio signal captured by a sound capture unit;
reducing a noise contained in the first captured audio signal obtained in the obtaining;
generating, based on a result of learning using a second captured audio signal obtained before the first captured audio signal, a target sound signal corresponding to the first captured audio signal;
determining an output mode to be applied among a plurality of output modes including a first output mode where the target sound signal corresponding to the first captured audio signal generated in the generating is output, and a second output mode where a noise-reduced signal obtained by reducing noise from the first captured audio signal in the reducing is output; and
outputting a signal according to the determined output mode determined in the determining.

2. The apparatus according to claim 1, wherein the apparatus further performs:
repeatedly performing no negative matrix factorization on a captured audio signal stored in a storage, thereby learning a spectral basis of the captured audio signal,
wherein, in the generating, a basis activate is calculated for generating the target sound signal by performing nonnegative matrix factorization on the captured audio signal by using the learned spectral basis; and
wherein, in the determining, the output mode is determined according to a magnitude of a coefficient of the basis activate output in the generating.

3. The apparatus according to claim 2, wherein the apparatus further performs:
estimating a noise signal from a captured audio signal obtained in the obtaining; and
deciding a division frequency at which the captured audio signal is divided into a low band and a high band according to a spectral distribution of the estimated noise signal,
wherein in the generating, the basis activate is calculated by performing nonnegative matrix factorization on the captured audio signal, based on a spectral basis above the division frequency decided in the deciding.

4. The apparatus according to claim 3, wherein in the case where a third output mode is determined to be applied in the determining, a low-band component of the noise-reduced signal that is below the division frequency is replaced with a low-band component of the target sound signal, according to a magnitude of a coefficient of the basis activate output in the generating, and a resulting signal is output in the outputting.

5. The apparatus according to claim 3, wherein in the case where a third output mode is determined to be applied in the determining, a low-band component of the target sound signal is mixed with a low-band component of the noise-reduced signal that is below the division frequency, according to a magnitude of a coefficient of the basis activate output in the generating, and a resulting signal is output in the outputting.

6. The apparatus according to claim 1, further comprising a plurality of the sound capture units, wherein the apparatus further performs estimating a noise signal from the captured audio signals captured by the plurality of the sound capture units, by using one of a beam former and independent component analysis, and wherein, in the reducing, the noise based on the noise signal estimated in the estimating is reduced.

7. The apparatus according to claim 1, wherein, in the reducing, the noise contained in the captured audio signal is reduced by using one of spectral subtraction, a high-pass filter, and a Wiener filter.

8. The apparatus according to claim 1, wherein in the determining, the output mode to be applied is determined among the plurality of output modes including the first mode, the second mode, and a third mode where a mixed signal obtained by mixing the target sound signal and the noise-reduced signal.

9. The apparatus according to claim 1, wherein the apparatus further performs:

detecting whether an amount of noise contained in a captured signal obtained in the obtaining is less than a predetermined amount; and storing the second captured audio signal, in a case where it is detected in the detecting that an amount of noise contained in the second captured audio signal is less than the predetermined amount, wherein, in the generating, the target sound signal corresponding to the first captured audio signal is generated based on the result of learning using a captured audio signal stored in the storing.

10. The apparatus according to claim 1, wherein the apparatus further performs:

estimating a noise signal from a captured audio signal captured from the sound capture unit;

detecting whether an estimated noise signal is in a noiseless state; and if it is detected that the estimated noise signal is in the noiseless state, analyzing the captured audio signal, and learning and modeling a characteristic obtained by the analysis, thereby generating a target sound model.

11. The apparatus according to claim 1, wherein:

in the reducing, a noise contained in the first captured audio signal is reduced, based on the estimated noise signal, wherein the target sound signal is generated by modeling the second captured audio signal by using the target sound model, and wherein, in the determining, the output mode to be applied is determined among the plurality of output modes including the first output mode, the second output mode, and a third output mode where a mixed signal obtained by mixing the target sound signal and the noise-reduced signal.

12. The apparatus according to claim 11, wherein in the determining, one of the first output mode, the second output mode, and the third output mode is selected according to an activation level of the target sound model.

13. The apparatus according to claim 11, wherein, in the detecting, if an average of absolute values of time amplitudes of the estimated noise signal in a processing unit frame is less than or equal to a predetermined threshold, it is detected that a time interval of the processing unit frame is in the noiseless state.

14. The apparatus according to claim 11, wherein, in the detecting, if a degree of correlation between captured audio signals respectively captured from a plurality of the sound capture units in a processing unit frame is greater than a predetermined threshold, it is detected that a time interval of the processing unit frame is in the noiseless state.

15. The apparatus according to claim 1, wherein, in the estimating, the noise signal is estimated from captured audio signals captured by a plurality of sound capture units by using one of a beam former and independent component analysis.

16. The apparatus according to claim 11, wherein, in the reducing, the noise contained in the first captured audio signal is reduced by using one of spectral subtraction, a high-pass filter, and a Wiener filter.

17. A method for controlling an apparatus comprising a hardware processor and a memory which stores the instructions to be executed by the hardware processor, wherein in accordance with the instructions executed by the hardware processor, the apparatus performs the method comprising:

obtaining a first captured audio signal captured by a sound capture unit;

reducing a noise contained in the first captured audio signal obtained in the obtaining;

generating, based on a result of learning using a second captured audio signal obtained before the first captured audio signal, a target sound signal corresponding to the first captured audio signal;

determining an output mode to be applied among a plurality of output modes including a first output mode where the target sound signal corresponding to the first captured audio signal generated in the generating is output and a second output mode where a noise-reduced signal obtained by reducing noise from the first captured audio signal in the reducing is output; and outputting a signal according to the determined output mode.

18. The method according to claim 17 further comprising:

estimating a noise signal from a captured audio signal input from the sound capture unit;

detecting whether an estimated noise signal is in a noiseless state; and if it is detected that the estimated noise signal is in the noiseless state, analyzing the captured audio signal, and learning and modeling a characteristic obtained by the analysis, thereby generating a target sound model.

19. A non-transitory computer-readable storage medium having stored therein instructions for controlling an apparatus comprising a hardware processor, wherein in accordance with the instructions executed by the hardware processor, the apparatus performs:

obtaining a first captured audio signal captured by a sound capture unit;

reducing a noise contained in the first captured audio signal obtained in the obtaining generating, based on a result of learning using a second captured audio signal obtained before the first captured audio signal, a target sound signal corresponding to the first captured audio signal;

determining an output mode to be applied among a plurality of output modes including a first output mode where the target sound signal corresponding to the first captured audio signal generated in the generating is output and a second output mode where a noise-reduced signal obtained by reducing noise from the first captured audio signal in the reducing is output; and outputting a signal according to the determined output mode.

20. The non-transitory computer-readable storage medium according to claim 19, wherein in accordance with the instructions executed by the hardware processor, the apparatus further performs:

estimating a noise signal from a captured audio signal captured from the sound capture unit;

detecting whether an estimated noise signal is in a noiseless state; and if it is detected that the estimated noise signal is in the noiseless state, analyzing the captured audio signal, and learning and modeling a characteristic obtained by the analysis, thereby generating a target sound model.

* * * * *